(12) United States Patent
Bedue et al.

(10) Patent No.: US 6,375,967 B1
(45) Date of Patent: Apr. 23, 2002

(54) REGENERATED CELLULOSE-BASED CELLULAR MATERIAL WITH A LONG-TERM RESISTANCE TO MICROORGANISMS, AND ITS PREPARATION

(75) Inventors: Olivier Bedue, Paris; Christophe Chalvin, Beauvais, both of (FR)

(73) Assignee: Financiere Elysees Balzac, Paris (FR)

( * ) Notice: Subject to any disclaimer, the term of this patent is extended or adjusted under 35 U.S.C. 154(b) by 0 days.

(21) Appl. No.: 09/688,353

(22) Filed: Oct. 16, 2000

Related U.S. Application Data

(63) Continuation of application No. 09/110,411, filed on Jul. 6, 1998, now abandoned.

(30) Foreign Application Priority Data

Jul. 7, 1997 (FR) ............................................ 97 08580

(51) Int. Cl.[7] ........................ A01N 25/00; A01N 25/08; A01N 25/34; A61K 31/015
(52) U.S. Cl. ...................... 424/405; 424/409; 424/411; 424/413; 514/764; 523/122
(58) Field of Search ................................ 424/405, 409, 424/411, 413; 514/764; 523/122

(56) References Cited

U.S. PATENT DOCUMENTS 5,817,325 A * 10/1998 Sawan et al. ................ 424/411
5,849,311 A * 12/1998 Sawan et al. ................ 424/406

OTHER PUBLICATIONS

Colin et al. (CA 113:99877, abstract of EP 358,572), Mar. 14, 1990.*

Bedue, O et al. (AN 1999–072632 WPIDS, abstract of FR 2765469), Jul. 7, 1997.*

* cited by examiner

*Primary Examiner*—Barbara P. Badio
(74) *Attorney, Agent, or Firm*—Bacon & Thomas

(57) ABSTRACT

The present invention relates to a regenerated cellulose-based cellular material with a long-term resistance to microorganisms—bacteria and/or fungi—and to a process for its preparation. Said material, which is of the sponge or sponge-cloth type, contains in its cellulosic bulk an effective amount of 2,4,4'-trichloro-2'-hydroxydiphenyl ether (triclosan) which is distributed and not enclosed in a matrix. At least one latex and advantageously at least one cationic compound are used together with said triclosan.

23 Claims, No Drawings

REGENERATED CELLULOSE-BASED CELLULAR MATERIAL WITH A LONG-TERM RESISTANCE TO MICROORGANISMS, AND ITS PREPARATION

This application is a Continuation of nonprovisional Ser. No. 09/110,411 filed Jul. 6, 1998 now abandoned.

The present invention relates to a regenerated cellulose-based cellular material with a long-term resistance to microorganisms—bacteria and/or fungi—and to a process for its preparation.

The present invention relates very particularly to sponges (voluminous cellular cellulosic products) and sponge-cloths (flat cellular cellulosic products (generally with a thickness less than or equal to 10 mm and often of the order of 5 mm)), which are intended especially for cleaning tasks, household maintenance or body hygiene and which have effective and long-term protection against the action of microorganisms. Those skilled in the art are aware that, after wringing, this type of material always retains a certain amount of water in its pores, which, in the absence of an appropriate biocidal treatment, encourages the development of foul-smelling and unhealthy microorganisms. It is therefore desirable to give these materials a long-term biocidal capability to combat the microorganisms which are present either in their structure or in the water with which they are almost permanently impregnated.

The base substrate of the materials of the invention is artificial sponge as obtained by the viscose process described especially in patent application FR-A-812 502. This process, which is familiar to those skilled in the art, is described in detail later in the present text with reference to the process for the preparation of the materials of the invention. Said process is based on a chemical modification of the cellulosic starting material. (Said cellulosic starting material, in this case wood pulp initially converted to alkaline cellulose, reacts with carbon disulfide to give cellulose xanthate, which is soluble in aqueous soda solution). The cellulose modified in this way (converted to one of its derivatives) has to be regenerated at the end of said process. The regeneration is carried out under harsh temperature and pH conditions.

According to the prior art, various methods have already been proposed for imparting long-term biocidal properties to cellular substrates based on regenerated cellulose.

These methods comprise the introduction and fixing of biocide(s) within the cellulosic structure of said substrates. Said introduction can be effected:

before the regeneration step; in this case, however, it is necessary to prevent the biocide from being released and/or destroyed during said regeneration;

after regeneration; the biocide can only be introduced if it is soluble or dispersible in an aqueous solution; in this case it is then essential to fix it in the porous structure so as to prevent it from being released during the first uses.

According to the prior art, it has been proposed in particular to introduce a biocidal agent into the semi-finished product (after regeneration of the cellulose). Said agent is fixed in the cellulose network either by precipitation—this technique is illustrated in patents U.S. Pat. No. 3,018,192, FR-A-1 200 663 and FR-A-1 345 614—or by a technique which combines precipitation with binding—the latter technique is illustrated in patent application EP-A-0 358 572 (the cellulosic product obtained contains the biocide, in solid form, mechanically trapped in a binder)—. The different variants of this method are adapted to cellulosic cellular products. However, insofar as they are based on precipitation, they impose the use of biocides capable of carrying a cationic charge, and post-treatments which can be expensive.

It has also been proposed:

to generate in situ a metal complex based on three components:
  a chelating polymer and more particularly chitosan;
  a transition metal (especially Zn) ion capable of forming a chelate with said chelating polymer; and
  an anti-microbial agent capable of forming a chelate with said transition metal ion, and more particularly an alkyl dithiocarbamate, a thiazole, an imidazole or a pyrithione (or one of its salts).

In general, said polymer and said anti-microbial agent are respectively introduced upstream and downstream of the cellulose regeneration step. This complex technique has been described in WO-A-94 12034;

to introduce the biocidal agent, before regeneration of the cellulose, in the form of particles enclosed in a matrix (<<in protected form>>). The matrix of said particles, loaded with biocidal agent, serves a dual purpose:
  it enables said biocidal agent to withstand the harsh conditions of the regeneration; and
  it makes it possible to control the rate of release of said biocidal agent.

This technique has been described by the Applicant in EP-A-617 074;

to introduce a particular biocidal agent together with a binder, in the process of manufacture of sponges. Said particular biocide is introduced in the viscose, in solution in an organic solvent or in a mixture with a surfactant, upstream of the regeneration in basic medium (before the porophoric agent). This technique is described in JP-A-47 50867. For its implementation, the inventors explicitly excluded many biocides, including pentachlorophenol, and therefore implicitly excluded triclosan (which belongs to the same family of chlorinated derivatives of phenol and which possess physico-chemical characteristics which are close to those of said pentachlorophenol). Said inventors only retained bis(tributyltin) oxide and tributyltin fluoride.

More generally, the introduction of biocides has been described in contexts which are different to that of the manufacture of artificial cellular cellulosic products.

The following has notably been described:

in DE-A-32 14610, synthetic fibers known as anti-microbial fibers, obtained by the melting of a mass, dissolution of the anti-microbial agent in said mass and melting and spinning. The synthetic fibrous material obtained is totally unconnected with the products of the invention. The process for its manufacture is totally unconnected with the process of the invention (melting/solubilisation and then regeneration);

in EP-A-0 709 507, the introduction of a biocide during the manufacture of a latex and the use of said latex thus loaded with said biocide for the binding of nonwovens;

in DE-A-1 288 747, synergistic biocide combinations. Said combinations are described per se, with reference to the biocidal efficiency. The problem of the fixing of a biocide or a combination of biocides to any substrate is not addressed;

in BE-A-644 153, a process for the protection of organic materials against micro-organisms. According to a variant of said process, the biocidal products—1-phenoxy-2-hydroxybenzenes—are introduced into said materials. The means of introduction are not described in detail for every type of material cited. In particular, no indication is found which refers to artificial cellulosic cellular materials, nor are any precision found as to the means of fixing, in general, of the biocidal products introduced, as to the stability of said fixing, as to the durability of the protection imparted etc. Only the introduction of triclosan is illustrated, in non-fibrous viscose, prior to the acidic regeneration of said viscose, to obtain films of regenerated cellulose which as such possess a good resistance to bacterial attack.

With reference to the technical problem of the effective and long-term protection of regenerated cellulose-based cellular materials against the action of microorganisms, the Applicant proposes, within the framework of the present invention, an original solution which is based on the choice of a particular biocide and on its means of fixing within the cellulosic matrix. Said original solution is suitable both for sponges and sponge-cloths despite the conditions for obtaining said sponges and sponge-cloths (see later on) being substantially different.

The selected biocide is interesting from several points of view:

it is per se a very high-performance product: it is effective at reasonable doses, it is non-toxic, it has a broad spectrum, etc.;

by virtue of its physico-chemical characteristics, it can be used in cellular cellulosic materials without being conditioned and, more particularly, without being enclosed in a matrix; and by virtue of its physico-chemical characteristics, it is capable of being trapped within said materials so as to exert a long-term action therein.

According to its first object, the present invention therefore relates to regenerated cellulose-based cellular materials which contain, in a stable manner, an effective amount of said biocide and, more precisely, to regenerated cellulose-based cellular materials of the sponge or sponge-cloth type which have a long-term resistance to microorganisms insofar as they characteristically contain, in their cellulosic bulk, an effective amount of 2,4,4'-trichloro-2'-hydroxydiphenyl ether which is distributed and not enclosed in a matrix, as well as an effective amount of at least one binder selected from the latexes.

The materials of the invention, of the sponge or sponge-cloth type, are used as such or integrated into a more complex structure, especially of the composite type. Such structures of the composite type have been described in the prior art, especially cleaning composites in patent application EP-A-500 460 and drying composites in patent application FR-A-2 680 670. Within the framework of the present invention, such composites are made with sponges and sponge-cloths which have long-term protection against microorganisms insofar as they contain an effective amount of 2,4,4'-trichloro-2'-hydroxydiphenyl ether and an effective amount of at least one binder.

Said 2,4,4'-trichloro-2'-hydroxydiphenyl ether, which has the following chemical formulae:

empirical formula: $C_{12}H_7Cl_3O_2$ structural formula:

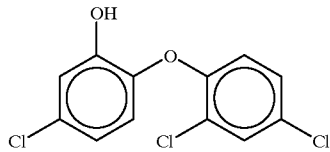

is known by the name triclosan. It takes the form of a white powder at room temperature.

This biocide is marketed by CIBA SPECIALITES CHIMIQUES under the trade mark IRGASAN DP 300®. Hitherto it has been used more particularly in the sectors of household maintenance products and cosmetic products and also for treating textiles, especially nonwovens.

Characteristically, the Applicant recommends its use, in a form not enclosed in a matrix, within the cellulosic bulk of regenerated cellulose-based materials. In non-obvious manner, such a use has proved not only possible but particularly appropriate, especially for the reasons stated above.

Said triclosan is generally distributed uniformly (see below its mode of use in the process for the production of the cellular cellulosic materials) in an amount of between 0.001 and 10% by weight, based on the weight of dry cellulose. In fact, an amount of 0.05 to 5% by weight, based on the weight of dry cellulose, is generally sufficient and it is recommended within the framework of the present invention to use an amount advantageously of only 0.2 to 2% by weight (based on the weight of dry cellulose).

The amount used is not really critical and it can be optimized by those skilled in the art.

As regards the stability and efficacy of said triclosan within the materials of the invention, it is far superior to that of numerous biocides insofar as, in particular, said triclosan is a chemical compound which is very poorly soluble in aqueous media and insensitive to anionic surfactants.

Said stability of said triclosan within the material of the invention is valued both in terms of its losses during regeneration, when it is introduced upstream of said regeneration, and in terms of its losses during the first uses of said material (whether it has been introduced upstream and/or downstream of said regeneration).

In order to optimize said stability, to chemically and/or physically bind said triclosan more strongly to the cellulose network, at least one binder of the latex type is used in the process for the production of the materials of the invention. In addition to said latex, at least one cationic compound may optionally be used. The conditions of use of these binder(s) and cationic compound(s) are specified later in the present text with reference to the process for the production of the materials of the invention.

Thus, according to the invention, the regenerated cellulose-based cellular materials contain the following in addition to said triclosan:

an effective amount of at least one binder selected from latexes and advantageously latexes whose polymer contains acrylonitrile groups (the latter type of latex has proved particularly effective at reasonable doses which barely affect the hydrophilicity of the materials of the invention); even furthermore:

an effective amount of at least one cationic compound. The use of such a cationic compound is very particularly advantageous within the structure of the voluminous cellular cellulosic materials of the invention, namely sponges.

The amounts used and the nature of the binders used and the cationic compounds which can be used, are specified below without in any way implying a limitation.

The latex-type binder can notably be selected from acrylic latexes, vinylic latexes, butadiene-styrene latexes, butadiene-styrene-acrylonitrile latexes, butadiene-acrylonitrile latexes and mixtures thereof. It has been seen that the use of latex the polymer of which contains acrylonitrile groups, is highly recommended.

The latex-type binder (or mixture of such binders) is generally introduced up to 10% by weight, more generally of between 0.5 and 5% by weight and advantageously of between 2 and 4% by weight. Said percentages by weight are understood as meaning percentages by weight of dry latex based on the weight of dry cellulose. The use of a large amount of latex would obviously detract from the hydrophilic character of the final product.

Within the materials of the invention, the function of the latex is not limited in any way to a mechanical trapping of the biocide insofar as the Applicant has noted that said biocide is perfectly fixed when it is introduced, in the process of preparation of the materials (see further on), downstream of said latex, even after the cross-linking of said latex by heating. Within the materials of the invention, the biocide/latex interaction thus seems to be based on physicochemical forces of the Van der Waals type.

The cationic compound (or mixture of cationic compounds) can generally be used in an amount of up to 5% by weight and more generally of between 0.05 and 2% by weight, based on the weight of dry cellulose. Particularly advantageously it is used in slight stoichiometric excess relative to the triclosan. The use of a larger amount has scarcely any effect insofar as the amount added in excess is inexorably eliminated during the first uses of the product in an aqueous medium.

Within the framework of the present invention, the Applicant (by conducting comparative tests, i.e. by comparing the residual amount of triclosan after different ageing cycles in products of the invention containing such additives and in products of the invention devoid of such additives) has also demonstrated in particular the positive action of:

aqueous dispersions of a copolymer based on butyl acrylate and acrylonitrile (and particularly the aqueous dispersion marketed under the name ACRONAL 32 D® by BASF);

aqueous dispersions of a copolymer based on butadiene and acrylonitrile (and particularly the aqueous dispersion marketed under the name PERBUNAN 2890® by BAYER);

a compound possessing a biguanide unit (and particularly polyhexamethylenebiguanide hydrochloride, or PHMB, marketed especially in the form of an aqueous solution under the name VANTOCIL IB® by ZENECA BIOCIDES);

dehydroabietylamine or its acetate (RAD); and a quaternary ammonium compound (and particularly N—($C_{12}$-$C_{14}$)alkyl-N,N-dimethyl-N-benzylammonium chloride, or AMBC, marketed especially in the form of a solution under the name PREVENTOL R 50® by BAYER).

The performance characteristics of materials of the invention are shown in the Examples section following the present description.

It is now proposed to describe the second subject of the present invention, namely a process for the preparation of the materials described above, said process being based on the viscose process of the prior art, where, characteristically, triclosan, at least one latex and optionally at least one cationic compound are introduced at one or more stages.

In general terms, said process comprises:

the preparation of a pulp from viscose and especially fibrous materials, an effective amount of porophoric agent(s) and optionally an effective amount of pigment (s);

the shaping of this pulp; and the heat treatment thereof, in an acid or basic medium, so that the action of said porophoric agent(s) is exerted and the cellulose is regenerated.

Each of said steps is described to some extent below.

The pulp is prepared especially from:

1) a basic solution of cellulose xanthate or viscose (said viscose being obtained by the action of an alkaline solution on the base cellulosic pulp, said action converting said cellulosic pulp to alkaline cellulose; the latter reacts with carbon disulfide to form a cellulose xanthogenate, which is solubilized in aqueous soda solution);

2) fibrous materials, such as cotton, sisal and flax, whose purpose is to increase the mechanical strength of the finished product;

3) generally pigments as well, the purpose of which is to give said finished product its color; and 4) porophoric agents like Glauber's salt (sodium sulfate decahydrate), which are soluble and/or fusible crystalline materials whose purpose is to form pores after coagulation of said pulp by digestion and/or fusion.

In principle, the fibrous materials are added to the viscose in a first stage. The pigments and porophoric agents are not added until afterwards. Said pulp can be shaped in particular by molding (in the context of sponges) or coating on either side or on only one side of at least one grid or deposition on a carrier strip (in the context of sponge-cloths).

As far as the heat treatment is concerned, it can be carried out in accordance with three main variants, which are respectively described as electrical regeneration, acidic regeneration and vapor regeneration.

According to the first of said variants—electrical regeneration—the heating is effected by passing an alternating electric current between electrodes held in contact with the pulp. This variant is especially developed in the context of the manufacture of sponges. In this case, in view of the chemical composition of the pulp, the heat treatment is carried out in a basic medium.

In the other two variants—acidic regeneration and vapor regeneration—the pulp is heated in so-called regeneration baths. Said pulp is brought into contact:

either with an acid medium (pH below 1), at temperatures of between 50 and 70° C., for a few minutes (so-called acidic regeneration, which advantageously utilizes a mixture of sulfuric acid and sodium sulfate, for the manufacture of sponge-cloths), or with a basic medium (pH around 10), at temperatures of about 100° C., for a few hours (so-called vapor regeneration, which advantageously utilizes a mixture of sodium hydroxide and sodium sulfate, for the manufacture of sponges).

In accordance with the conventional process, the resulting products—cellulosic cellular materials—are then rinsed, optionally bleached, dried and generally plasticized before being cut up and packaged.

Characteristically, according to the invention, provision is made, within the framework of this process of the prior art, for the use of triclosan which is not enclosed in a matrix, and for the use of a binder. Said triclosan is added:

- upstream and/or downstream of said heat treatment, when the latter is carried out in an acid medium (in the context of the manufacture of sponge-cloths); or
- downstream of said heat treatment, when the latter is carried out in a basic medium (in the context of the manufacture of sponges).

It is particularly advantageous to be able to introduce said triclosan upstream of said acidic regeneration.

Said triclosan is generally added all at once in the form of a soda solution.

It is used in an effective amount, especially an amount such as specified above.

Said process of the invention further comprises:

- the addition, (to the pulp) upstream of the heat treatment and/or (to the semi-finished product) downstream of the heat treatment, of an effective amount of at least one binder selected from latexes and advantageously latexes whose polymer contains acrylonitrile groups; and, optionally,
- the addition, (to the semi-finished product) downstream of the heat treatment, of an effective amount of at least one cationic compound.

In particular, said latex (latexes) can be introduced either during the preparation of the pulp (before regeneration, particularly when the pigments for coloring the final product are added to the pulp), or after regeneration of said pulp.

Within the framework of the process of the invention, the latex(es) can perfectly well be introduced after the biocide.

As far as the cationic compound(s) are concerned, it is recalled here that its (their) use is very particularly advantageous in the context of the manufacture of sponges. It proves appropriate to introduce it (them) after regeneration, advantageously after said triclosan and said latex. In the case where a plasticizing operation is carried out, the cationic compound is advantageously introduced together with the plasticizer if the two products are compatible or, advantageously, before said plasticizer if the two products are incompatible.

It is now proposed to describe in detail preferred modes of carrying out the process of the invention for the preparation of sponges on the one hand and sponge-cloths on the other.

In the case of sponges, the regeneration is effected in a basic medium and the semi-finished product is generally dried and/or plasticized. It has been seen that, in such a context, the triclosan is added downstream of the heat treatment. (Added upstream, it would dissolve in the basic regeneration bath). Said latex used can be added upstream and/or downstream of the (regenerative) heat treatment. It is advantageously added upstream of said heat treatment; when it is introduced downstream thereof, it is advantageously added before or at the same time as said triclosan. In order to optimize the <<fixing>> of said triclosan in the cellulosic network, it is advantageous, within the framework of this preferred mode, to introduce at least one cationic compound downstream of said heat treatment.

It has been seen in general terms that such a cationic compound is advantageously added after said latex and said triclosan and, when a plasticizing operation is carried out, the cationic compound is added just before said operation if it is incompatible with said plasticizer(s) used, or at the same time as said plasticizer(s) if they are compatible.

It is therefore very particularly preferred to produce the sponges of the invention by adding the latex upstream of the heat treatment and the triclosan downstream of said heat treatment.

In the case of sponge-cloths, the regeneration is effected in an acid medium and, in the same way, the semi-finished product is generally plasticized. It has been seen that, in such a context, the triclosan can be added either upstream or downstream of the regenerative heat treatment and that the use of cationic compound(s) proves less appropriate. Within the framework of the preferred mode described here, at least one latex is associated with said triclosan, it again being possible to introduce said latex either upstream or downstream of the regenerative heat treatment.

Within the framework of this preferred mode, said compounds are both advantageously introduced upstream of the heat treatment and, even more advantageously, the triclosan is introduced first: it is added to the viscose at the same time as the fibrous materials, and the latex is added afterwards to the pulp formed.

The plasticizing operation carried out on the sponge-cloths of the invention is advantageously almost a final stage. It is effected after the compounds of the triclosan and latex type have been added.

The present invention is illustrated by the Examples below.

Unless indicated otherwise, the percentages given in said Examples are by weight, based on the weight of dry cellulose.

A) Sponges

The Examples which follow relate to products of the sponge type into which the IRGASAN DP 300® has been introduced after the regeneration step.

In general:

The amounts of IRGASAN DP 300® present in the sponges were determined as specified below.

The plasticized products are successively compressed 20 times in 300 ml of distilled water and then in 2 times 300 ml of 0.1 N sodium hydroxide solution. The three solutions are combined and the amount of triclosan extracted is determined by UV spectrophotometry.

The unplasticized products are compressed 20 times in 300 ml of 0.1 N sodium hydroxide solution. The amount of triclosan extracted is determined by UV spectrophotometry.

The resistance of the treated products to bacterial attack is evaluated by introducing 2.5 grams of treated sponge into 200 ml of TCS broth which has previously been inoculated with a suspension of *Escherichia coli* so that the broth contains about $5.10^3$ CFU/ml. After incubation for 4 and 24 hours at 37° C., the bacterial population is determined. The grade "++" is assigned if the population is less than $5.10^4$ CFU/ml, the grade "+" is assigned if the population is between $5.10^4$ CFU/ml and $5.10^6$ CFU/ml and the grade "0" is assigned if the population is more than $5.10^6$ CFU/ml.

To simulate household use, the sponges are subjected to ageing cycles, after which the amount of IRGASAN DP 300® and the resistance to bacterial attack are measured. The cycle E60 consists in subjecting 3 sponges (weighing about 20 grams) to a washing machine cycle with spinning (450 rpm) at 60° C. without the introduction of detergent. The cycle F60 consists in subjecting 3 sponges (weighing about 20 grams) to a washing machine cycle with spinning (450 rpm) at 60° C. with the introduction of 92 grams of an industrial detergent (MATIC SPOT® detergent).

EXAMPLE A-1

Sponges of the invention are manufactured by the conventional process (viscose process with electrical coagulation), respectively 0, 2, 6 and 10% of ACRONAL 32 D® (an aqueous dispersion of a copolymer based on butyl acrylate and acrylonitrile, marketed by BASF) being introduced into the fiber-containing viscose (cellulose xanthate+ fibers). After basic regeneration, 1.3% of IRGASAN DP 300® (dissolved in sodium hydroxide) and 30% of magnesium chloride (plasticizer) in the form of a solution (said 30% being expressed as anhydrous $MgCl_2$) are introduced successively. The (residual) amounts of triclosan present in the products after the different ageing cycles are indicated in the Table below.

| Amount of ACRONAL 32 D ® introduced (%) | Amount of triclosan after an E60 cycle (%) | Amount of triclosan after an F60 cycle (%) |
| --- | --- | --- |
| 0 | 0.06 | 0.02 |
| 2 * | 0.12 | 0.03 |
| 6 * | 0.27 | 0.05 |
| 10 * | 0.47 | 0.07 |

* The percentages relative to the latex are understood in terms of commercial latex.

It is noted that the greater the amount of latex introduced, the more the triclosan is retained in the sponge.

EXAMPLE A-2

The tests described in Example 1 are repeated, respectively 6% of ACRONAL 32 D® and 7.3% of PERBUNAN 2890® (an aqueous dispersion of a copolymer based on butadiene and acrylonitrile, marketed by Bayer) (i.e., taking into account the dry extracts of the two dispersions, 3% of copolymer) being introduced into the fiber-containing viscose (cellulose xanthate+fibers). The sponges are treated in the same way as above for the introduction of IRGASAN DP 300®.

The (residual) amounts of triclosan present in the products after the different ageing cycles are indicated in the Table below.

| Nature of the latex | Amount of triclosan after an E60 cycle (%) | Amount of triclosan after an F60 cycle (%) |
| --- | --- | --- |
| ACRONAL 32 D ® | 0.27 | 0.05 |
| PERBUNAN 2890 ® | 0.37 | 0.07 |

PERBUNAN 2890 ® favors the fixing of the triclosan more than ACRONAL 32 D ®.

EXAMPLE A-3

Sponges are manufactured by the conventional process (viscose process with electrical coagulation), 6% of ACRONAL 32 D® being introduced into the fiber-containing viscose (cellulose xanthate+fibers). After basic regeneration, in a first stage IRGASAN DP 300® (in the form of a solution in sodium hydroxide) is introduced in the proportions specified in the Table below, and in a second stage a cationic compound is introduced, also in the proportions specified in said Table.

The cationic compounds used were PHMB (VANTOCIL IB® marketed by ZENECA BIOCIDES: poly (hexamethylenebiguanide) hydrochloride) and RAD (dehydroabietylamine acetate).

The results of the tests for evaluation of the resistance of the products to bacterial attack after different ageing cycles are collated in the Table below.

| Amount of triclosan introduced (%) | Nature of the cationic compound | Amount of cationic compound introduced (%) | Resistance to bacterial attack after an F60 cycle |
| --- | --- | --- | --- |
| 0.7 | — | — | 0 |
| 0.7 | PHMB | 0.53 | + |
| 0.7 | PHMB | 1.06 | + |
| 0.7 | PHMB | 1.59 | +/++ |
| 1 | — | — | 0 |
| 1 | RAD | 3.58 | + |
| 1.3 | — | — | + |

It is found that the addition of cationic compounds makes it possible significantly to increase the efficacy of the treatment.

EXAMPLE A-4

The tests described in Example 3 are repeated, a solution of magnesium chloride (plasticizer) being introduced at the same time as the cationic compound so that the sponge contains 30% of magnesium chloride (said 30% being expressed as anhydrous $MgCl_2$ and based on the weight of dry cellulose).

The cationic compound used is AMBC (PREVENTOL R 50® marketed by BAYER: N-alkyl-N,N-dimethyl-N-benzylammonium chloride).

The results of the tests for evaluation of the resistance of the products to bacterial attack after different ageing cycles are collated in the Table below.

| Amount of triclosan introduced (%) | Nature of the cationic compound | Amount of cationic compound introduced (%) | Resistance to bacterial attack after an E60 cycle | Resistance to bacterial attack after an F60 cycle |
| --- | --- | --- | --- | --- |
| 0.7 | — | — | + | 0 |
| 0.7 | AMBC | 1.02 | +/++ | +/++ |
| 0.5 | AMBC | 0.73 | +/++ | + |

An improvement in the protection of the cellulosic sponge is observed, even in the presence of magnesium chloride.

B) Sponge-cloths

The Examples which follow relate to products of the sponge-cloth type into which the IRGASAN DP 300® has been introduced before the (acidic) regeneration step.

In general:

The amounts of IRGASAN DP 300® present in the sponge-cloths were determined in the following manner:

The products are left to stand in 0.1 N sodium hydroxide solutions for 24 hours. The amount of triclosan extracted is determined by UV spectrophotometry.

The resistance of the treated products to bacterial attack is evaluated by introducing, into a 2-gram disk of sponge-cloth, 4 ml of TCS broth which has previously been inoculated with a suspension of *Escherichia coil* so that the broth contains about $10^5$ CFU/ml. The impregnated sample is then deposited on an agar. After incubation for 48 hours at 37° C., the bacterial population is determined visually. The grade "+" is assigned if the growth is totally inhibited, the grade "+/−" is assigned if a few strains are observable where the agar is in contact with the sample, and the grade "−" is assigned if the sample is totally colonized.

To simulate household use, the sponge-cloths are subjected to ageing cycles, after which the amount of IRGASAN DP 300® and the resistance to bacterial attack are measured. The cycle D consists in expressing the product 200 times into a solution containing the dishwashing product PAIC® (at a rate of 0.5 g of product per liter of solution). The cycle E60 consists in subjecting 1 sponge-cloth (weighing about 11 grams) to a washing machine cycle with spinning (450 rpm) at 60° C. without the introduction of detergent. The cycle F60 consists in subjecting 1 sponge-cloth (weighing about 11 grams) to a washing machine cycle with spinning (450 rpm) at 60° C. with the introduction of 92 grams of an industrial detergent (MATIC SPOT® detergent). The cycle F20 is identical to the cycle F60 except that the temperature is lowered to 20° C.

The results shown in the two Tables below (Examples B-1 to B-6) were obtained after carrying out tests during which:

the IRGASAN DP 300® is introduced into the cellulose xanthate at the same time as the reinforcing fibers, which are used in the form of a dispersion in sodium hydroxide solution; and the latex used is ACRONAL 32 D®. It is introduced into the fiber-containing viscose (mixture of cellulose xanthate and fibers) after the biocide. The porophoric crystals are not added until after said latex. It is noted, upon considering Examples B-1 and B-2 on the one hand, and B-3 and B-4 on the other, how much the use of said latex is advantageous.

The two ingredients—biocide and latex—are introduced before the regeneration step.

The initial percentages (amounts used) of biocide and latex are expressed relative to the weight of dry cellulose in the product. The levels of residual biocide are expressed relative to the amount of biocide initially introduced.

| Example | Amount of triclosan introduced (%) | Amount of latex introduced (%) | after regeneration | after a D cycle | after an E60 cycle | after an F20 cycle | after an F60 cycle |
|---|---|---|---|---|---|---|---|
| | | | Amount of triclosan (%) | | | | |
| B-1 | 0.5 | 0 | 70 | 27 | 5 | 3 | 2 |
| B-2 | 0.5 | 3 | 88 | 40 | 6 | | 1 |
| B-3 | 1 | 0 | 60 | 30 | 10 | | 1 |
| B-4 | 1 | 2 | 95 | 65 | 15 | 6 | 0 |
| B-5 | 2 | 5 | 98 | 68 | 40 | 37 | 1 |
| B-6 | 2 | 3 | 95 | 67 | 35 | 25 | 2 |
| | | | Biocidal efficacy | | | | |
| B-1 | 0.5 | 0 | + | + | − | − | − |
| B-2 | 0.5 | 3 | + | + | − | − | − |
| B-3 | 1 | 0 | + | + | + | − | − |
| B-4 | 1 | 2 | + | + | + | +/− | − |
| B-5 | 2 | 5 | + | + | + | + | − |
| B-6 | 2 | 3 | + | + | + | + | +/− |

What is claimed is:

1. Regenerated cellulose-based cellular material of the sponge or sponge-cloth type with a long-term resistance to microorganisms, which contains in its regenerated cellulosic bulk, an effective amount of 2,4,4'-trichloro-2'-hydroxydiphenyl ether (triclosan) which is distributed and not enclosed in a matrix, and an effective amount of at least one binder selected from the latexes.

2. The material according to claim 1, which contains from 0.001 to 10% by weight, of said triclosan, based on the weight of dry cellulose.

3. The material according to claim 1, wherein said binder is selected from the latexes whose polymer contains acrylonitrile groups.

4. The material according to claim 1, wherein said binder is used in an amount of up to 10% by dry weight, based on the weight of dry cellulose.

5. The material according to of claim 1, which also contains an effective amount of at least one cationic compound.

6. The material according to claim 5, wherein said cationic compound is used in an amount of up to 5% by weight, based on the weight of dry cellulose.

7. The material according to claim 5, wherein said cationic compound is used in slight stoichiometric excess relative to the triclosan.

8. The material according to claim 1 which contains from 0.05 to 5% by weight of said triclosan, based on the weight of dry cellulose.

9. The material according to claim 1, which contains from 0.2 to 2% by weight of said triclosan, based on the weight of dry cellulose.

10. The material according to claim 4, wherein said binder is used in an amount of between 0.5 and 5% by weight, based on the weight of dry cellulose.

11. The material according to claim 4, wherein said binder is used in an amount of between 2 and 4% by weight, based on the weight of dry cellulose.

12. The material according to claim 6, wherein said cationic compound is used in an amount of between 0.05 and 2% by weight, based on the weight of dry cellulose.

13. The regenerated cellulose-based cellular material of claim 1 wherein said triclosan is not mechanically entrapped within said latex but said triclosan is distributed within the cellulosic material and retained therein by said latex via Van der Waals Chemical Forces.

14. A process for the preparation of a material according to claim 1, comprising:

preparing a pulp from viscose, fibrous material, an effective amount of porophoric agent(s) and optionally an effective amount of pigment(s);

shaping said pulp;

heat treating said pulp which has been shaped, said heat treatment being conducted in an acid or basic medium so that the action of said porophoric agent(s) is exerted and the cellulose is regenerated to produce a semifinished product;

adding an effective amount of 2,4,4'-trichloro-2'-hydroxydiphenyl ether (triclosan) not enclosed in a matrix, said triclosan being added upstream and/or downstream of said heat treatment when said heat treatment is carried out in an acid medium; or downstream of said heat treatment when said heat treatment is carried out in a basic medium; and adding an effective amount of at least one binder selected from the latexes, said binder being added upstream and/or downstream from said heat treatment step.

15. The process of claim 14 wherein said binder is latex polymer containing acrylonitrile groups.

16. The process of claim 14 which further comprises adding an effective amount of at least one cationic compound; said at least one cationic compound being added downstream of said heat treatment step.

17. The process of claim 16 for the preparation of a sponge with a long term resistance to microorganisms, wherein:

said pulp is shaped by molding;

said heat treating is carried out in a basic medium and said triclosan is added downstream of the heat treating step;

said process optionally further includes drying and/or plasticizing the semi-finished product obtained by the regeneration of said cellulose;

with the proviso that when said plasticizing operation is carried out,
  a) the addition of said triclosan is effected before or at the same time as the plasticizing operation; and
  b) said at least one cationic compound is added after the addition of said latex and said triclosan just before the plasticizing operation if said at least one cationic compound is compatible with plasticizer(s) used in said plasticizing operation, or said at least one cationic compound is added at the same time as said plasticizer(s) if said at least one cationic compound is compatible with said plasticizer(s).

18. The process of claim 17 wherein said latex is added upstream of said heat treating step.

19. The process of claim 17 wherein said latex is introduced downstream of said heat treating step.

20. The process of claim 19 wherein said latex is added before or at the same time as said triclosan.

21. The process of claim 14 for the preparation of a sponge-cloth with a long-term resistance to microorganisms wherein:
  said pulp is shaped by coating said pulp on either side or on only one side of a grid or by deposition on a carrier strip;
  said heat treating is carried out in an acid medium;
  said triclosan and said latex are both added upstream of said heat treating step.

22. The process of claim 21 wherein said triclosan is added to said viscose at the same time as the fibrous material and said latex is added after the preparation of said pulp.

23. The product obtained by the process of claim 14 wherein said triclosan is not enclosed in a matrix and is not mechanically entrapped by said latex but is distributed within the cellulosic material and retained therein by the latex via Van der Waals Chemical Forces.

* * * * *